(12) United States Patent
Fischetti et al.

(10) Patent No.: US 7,063,837 B2
(45) Date of Patent: *Jun. 20, 2006

(54) SYRUP COMPOSITION CONTAINING PHAGE ASSOCIATED LYTIC ENZYMES

(75) Inventors: Vincent Fischetti, West Hempstead, NY (US); Lawrence Loomis, Columbia, MD (US)

(73) Assignees: New Horizons Diagnostics Corp, Columbia, MD (US); Rockefeller University, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/908,737

(22) Filed: Jul. 19, 2001

(65) Prior Publication Data

US 2002/0127206 A1    Sep. 12, 2002

Related U.S. Application Data

(63) Continuation-in-part of application No. 09/752,731, filed on Jan. 3, 2001, now abandoned, and a continuation-in-part of application No. 09/482,992, filed on Jan. 14, 2000, now Pat. No. 6,264,945.

(51) Int. Cl.
*A61K 38/00* (2006.01)

(52) U.S. Cl. .................... 424/94.1; 424/93.6; 514/774; 514/777

(58) Field of Classification Search .................. 424/45, 424/46, 50, 78.02, 78.04, 78.06, 78.03, 94.1, 424/94.61, 422, 427, 430, 431, 436, 439, 424/440, 441, 442, 443, 435, 446, 447, 450, 424/451, 464, 489, 93.6, 449; 514/2, 936, 514/937, 947, 944, 948, 951, 962, 969, 774, 514/777; 435/195
See application file for complete search history.

(56) References Cited

U.S. PATENT DOCUMENTS

| | | | |
|---|---|---|---|
| 2,019,789 A | 11/1935 | Mahannah | |
| 2,315,260 A | 3/1943 | Lancaster | |
| 2,763,931 A | 9/1956 | McMillan | |
| 3,465,445 A | 9/1969 | Fisher | |
| 3,622,677 A | 11/1971 | Short et al. | |
| 3,852,424 A | 12/1974 | Gaeumann et al. | |
| 3,929,994 A | 12/1975 | Hirsch et al. | |
| 3,983,209 A | 9/1976 | Schmitt | |
| 4,062,941 A | 12/1977 | Davies | |
| 4,115,546 A | 9/1978 | Vidra et al. | |
| 4,116,327 A | 9/1978 | Eglinton et al. | |
| 4,122,158 A | 10/1978 | Schmitt | |
| 4,313,734 A | 2/1982 | Leuvering | |
| 4,355,022 A | 10/1982 | Rabussay | |
| 4,361,537 A | 11/1982 | Deutsch et al. | |
| 4,369,308 A | 1/1983 | Trubiano | |
| 4,459,361 A | 7/1984 | Gefter | |
| 4,497,900 A | 2/1985 | Abram et al. | |
| 4,521,252 A | 6/1985 | Miyake et al. | |
| 4,552,839 A | 11/1985 | Gould et al. | |
| 4,707,543 A | 11/1987 | Zollinger et al. | |
| 4,713,249 A | 12/1987 | Schroder | |
| 4,742,981 A | 5/1988 | Converse | |
| 4,784,948 A | 11/1988 | Scott et al. | |
| 4,812,445 A | 3/1989 | Eden et al. | |
| 4,847,199 A | 7/1989 | Snyder et al. | |
| 4,859,597 A | * 8/1989 | Yang et al. | .................. 435/239 |
| 4,885,163 A | 12/1989 | Shaar et al. | |
| 4,933,185 A | 6/1990 | Wheatley et al. | |
| 4,948,726 A | 8/1990 | Longoria | |
| 4,957,686 A | 9/1990 | Norris | |
| 5,079,174 A | 1/1992 | Buck et al. | |
| 5,108,758 A | 4/1992 | Allwood et al. | |
| 5,120,643 A | 6/1992 | Ching et al. | |
| 5,162,226 A | 11/1992 | Beachey et al. | |
| 5,260,292 A | 11/1993 | Robinson et al. | |
| 5,294,369 A | 3/1994 | Shigekawa et al. | |
| 5,352,588 A | 10/1994 | Fischetti et al. | |
| 5,360,617 A | 11/1994 | Gasson | |
| 5,372,931 A | 12/1994 | Friedman et al. | |
| 5,384,265 A | 1/1995 | Kidwell et al. | |
| 5,393,658 A | 2/1995 | Olsen | |
| 5,479,732 A | 1/1996 | Burtch et al. | |
| 5,500,350 A | 3/1996 | Baker et al. | |
| 5,514,602 A | 5/1996 | Brooks, Jr. et al. | |
| 5,556,944 A | 9/1996 | Fischetti et al. | |
| 5,571,667 A | 11/1996 | Chu et al. | |
| 5,587,288 A | 12/1996 | Cheung et al. | |
| 5,602,040 A | 2/1997 | May et al. | |
| 5,604,109 A | 2/1997 | Fischetti et al. | |
| 5,604,110 A | 2/1997 | Baker et al. | |
| 5,605,793 A | 2/1997 | Stemmer | |
| 5,616,686 A | 4/1997 | Fischetti et al. | |

(Continued)

FOREIGN PATENT DOCUMENTS

EP        0293249 A1    11/1988

(Continued)

OTHER PUBLICATIONS

Reisenger, et al. (1998) "Characterization of *Escherichia coli* lysis using a family of chimeric E-L Genes" *Fems Microbiol Letter.* 164(1) p. 159-167.

(Continued)

*Primary Examiner*—Francisco Prats
(74) *Attorney, Agent, or Firm*—Jonathan E. Grant; Grant Patent Services

(57) ABSTRACT

The present invention discloses a method and composition for the treatment of bacterial infections by the parenteral introduction of at least one lytic enzyme produced by a bacteria infected with a bacteriophage specific for that bacteria and an appropriate carrier for delivering the lytic enzyme into a patient. The injection can be done intramuscularly, subcutaneously, or intravenously.

19 Claims, No Drawings

U.S. PATENT DOCUMENTS

| | | | |
|---|---|---|---|
| 5,643,767 | A | 7/1997 | Fischetti et al. |
| 5,688,501 | A | 11/1997 | Merril et al. |
| 5,707,822 | A | 1/1998 | Fischetti et al. |
| 5,723,303 | A | 3/1998 | Fischetti et al. |
| 5,741,487 | A | 4/1998 | Asai et al. |
| 5,760,026 | A | 6/1998 | Blackburn et al. |
| 5,763,251 | A | 6/1998 | Gasson |
| 5,786,205 | A | 7/1998 | Fischetti et al. |
| 5,821,088 | A | 10/1998 | Darzins et al. |
| 5,840,314 | A | 11/1998 | Scott et al. |
| 5,882,631 | A | 3/1999 | Suga et al. |
| 5,910,441 | A | 6/1999 | Rocha et al. |
| 5,968,763 | A | 10/1999 | Fischetti et al. |
| 5,976,792 | A | 11/1999 | Cheung et al. |
| 5,985,271 | A | 11/1999 | Fischetti et al. |
| 5,985,654 | A | 11/1999 | Fischetti et al. |
| 5,997,862 | A | 12/1999 | Fischetti et al. |
| 6,017,528 | A | 1/2000 | Fischetti et al. |
| 6,056,954 | A | 5/2000 | Fischetti et al. |
| 6,056,955 | A | 5/2000 | Fischetti et al. |
| 6,083,684 | A | 7/2000 | Gasson |
| 6,113,887 | A | 9/2000 | Mori et al. |
| 6,132,970 | A | 10/2000 | Stemmer |
| 6,159,688 | A | 12/2000 | Borchert et al. |
| 6,177,554 | B1 | 1/2001 | Woo et al. |
| 6,187,757 | B1 | 2/2001 | Clackson et al. |
| 6,190,659 | B1 | 2/2001 | Pancholi et al. |
| 6,238,661 | B1 | 5/2001 | Fischetti et al. |
| 6,248,324 | B1 | 6/2001 | Fischetti et al. |
| 6,254,866 | B1 | 7/2001 | Fischetti et al. |
| 6,264,945 | B1 | 7/2001 | Fischetti et al. |
| 6,277,399 | B1 | 8/2001 | Fischetti et al. |
| 6,326,002 | B1 | 12/2001 | Fischetti et al. |
| 6,331,405 | B1 | 12/2001 | Rambukkana et al. |
| 6,335,012 | B1 | 1/2002 | Fischetti et al. |
| 6,355,477 | B1 | 3/2002 | Fischetti et al. |
| 6,399,097 | B1* | 6/2002 | Fischetti et al. ............ 424/464 |
| 6,399,098 | B1* | 6/2002 | Fischetti et al. ............ 424/464 |
| 6,406,692 | B1* | 6/2002 | Fischetti et al. ............ 424/94.1 |
| 6,423,299 | B1* | 7/2002 | Fischetti et al. ............ 424/45 |
| 6,432,444 | B1* | 8/2002 | Fischetti et al. ............ 424/443 |

FOREIGN PATENT DOCUMENTS

| | | |
|---|---|---|
| EP | 0359873 A1 | 3/1990 |
| EP | 0 510 907 A | 10/1992 |
| EP | 0510907 A 2 | 10/1992 |
| EP | 587541 A1 | 3/1994 |
| EP | 0646646 A2 | 4/1995 |
| FR | 2357246 | 2/1978 |
| WO | WO-9323544 | 11/1993 |
| WO | WO-9531562 | 11/1995 |
| WO | WO 96 07329 A | 3/1996 |
| WO | WO-9607329 | 3/1996 |
| WO | WO 97 02351 A | 1/1997 |
| WO | WO-9702351 | 1/1997 |
| WO | WO 99 04809 A | 2/1999 |
| WO | WO-9904809 | 2/1999 |

OTHER PUBLICATIONS

Sheehan MM, et al. (1997) "The lytic enzyme of the Phneumococcal Phage Dp-1: a chimeric lysis of intergeneric origin." *Mol. Microbiol.* 25(4) p. 717-725.

Young et al. (2000) "Phages will out: strageqies of host cell lysis." *Trends in Microbiology.* 8(4) p. 120-127.

Garcia et al.(1997) "The Pneumococcal cell wall degrading enzymes: A modular design to create new lysins?" *Microb. Drug Resist.* 3(2): p. 199-211.

Sheehan MM, et al., (1997) "The Lytic Enzyme of the Pneumococcal Phage Dp-1: a Chimeric Lysin on Intergeneric Origin" *Mol. Microbiol.* 25(4) p. 717-25.

Garcia P, et al. (1997) "Bacteriophages of Streptococcus pneumoniae: a molecular approach" *Microb. Drug Resist.* 3(20) 165-76.

Sheehan, MM, et al.(1996) "Analysis of the catalytic domain of the lysin of the lactococcal bacteriophage Tuc2009 by chimeric gene assembling." *FEMS Microbiol. Lett.* 14(1): p. 23-28.

Sanz, JM, et al. (1996) "Construction of a multifunctional pneumococcal murein hydrolase by module assembly." *Eur. J. Biochem.* 235(3):601-5.

Lopez R, et al. (1995) "Architecture and Domain Interchange of the Pneumococcal Cell Wall Lytic Enzymes" *Dev. Biol. Stand.* 85 p. 273-81.

Croux, et al.(1993) "Interchange of Functional Domains Switches Enzymes Specificity: Construction of a chimeric pneumococcal-clostridial cell wall lytic enzyme." *Mol. Microbiology.* 9(5) p. 1019-25.

Diaz, E. et al. (1990) Chimeric phage-bacterial enzymes: a clue to the modular evolution of genes. *PNAS.* 87(20) p. 8125-9.

Diaz, E. et al.(1990) "Chimeric pneumoccal cell wall lytic enzymes reveal important physiological and evolutionary traits." *J. Biol. Chem.*266(9) p. 5464-71.

Lopez, et al. (1997) "The pneumococcal cell wall degrading enzymes: A modular design to create new lysins?" *Microbiological Drug Resistance.* (3)2 p. 199-211.

Loessner, et al. (1999) "Evidence for a holin-like protein gene fully embedded out of frame in the endolysin gene of *Staphylococcus aureus* Bacteriophage." (1999) *Journal of Bacteriology.* 181(15) p. 4452-4460.

Witte, A et al. (1998) "Characterization of *Escherichia coli* lysis using a family of chimeric E-L genes." *FEMS Microbiol. Lett.*, 164(1), p. 159-167.

Martin, Ana C et al (1998): "Functional analysis of the two-gene lysis system of the pneumococcal phage Cp-1 in homologous and heterologous host cells." *Journal of Microbiology* 180(2), p. 210-217.

Oki Masaya et al. (1997) "Functional and structural features of the holin HOL protein of the Lactobacillus plantarum phage phi-gle: Analysis in *Escherichia coli* system." *Gene (AMSTERDAM)* 197(1-2) p. 137-145.

Young, Ry et al. (2000) "Phages will out: strategies of host cell lysis." *Trends in Microbiology*, 8(3) p. 120-127.

Nelson, et al. (2001) "Prevention and elimination of upper respiratory colonization of mice by Group A Streptococci by using a bacteriophage lytic enzyme." *PNAS.* 98 (7) p. 4107-4112.

Garcia, et al. (1987) "Purification and biochemical characterization of the pneumococcal bacteriophage Cp-1 lysin." *Journal of Virology* 61(8) p. 2573-2580.

Loessner, et al. (1996) "Modified Listeria bacteriophage lysin genes (ply) allow efficient overexpression and one-step purification of biochemically active fusion proteins." *Applied and Environmental Microbiology.* 62(8) p. 3057-6060.

KH Nasibulini et al; RU-2103991; Composition for treating streptococcal diseases—comprises purified concentrate of streptococcal bacteriophage, solution of quinsosol, dry lanolin, albumin and vegetable oil; XP-002141110.

LD Demidova et al; RU2064299; Cattle mastitis therapeutic preparation—comprises lyso: amidase of specific lytic activity and mono- and di-basic sodium phosphate(s); XP-002141111.

Babenko et al. Enzymatic lysis of staphylococci in relation to their species and strain properties, 1990, Datbase Medline Online, US National Library of Medicine, Bethesda, MD, US, Database Accession No. 90297672 XP002170795, abstract only.

Bartell, et al., Origin of polysaccharide depolymerase associated with bacteriophage infection. Journal of Virology, Mar. 1969, pp. 290-296, vol. 3, No. 3.

Behnke, et al., Cloning and expression in Escherichia coli, Bacillus subtilis and Streptococcus sanguis of a gene for staphylokinase—a bacterial plasminogen activator, Mol Gen Genet, Dec. 1987, pp. 528-534, vol. 210.

Bessen, et al., Chemical characterization of binding properties of opacity-associated protein II from Neisseria gonorrheae, Infection and Immunity, Jan. 1987, pp. 141-147, vol. 55, No. 1.

Biziulevichius, et al., In vivo studies on lysosubtilin: 3. Efficacy for treatment of mastitis and superficial lesions of the udder and teats in cows, 1998, Database Biosis Online, Biosciences Information Service, Philadelphia, PA, US, Database Accession No. PREV199800492606, XP002183274, abstract only.

Boizet, et al., Cloning, expression and sequence analysis of an endolysin-encoding gene of Lactobacillus bulgaricus bacteriophage mv1, Gene, 2000, pp. 61-67, vol. 94.

Caldwell, et al., Purification and partial charcterization of the major outer membrane protein of Chlamydia trachomatis, Infection and Immunity, Mar. 1981, pp. 1161-1176, vol. 31, No. 3.

Young et al. Phages will out: strategies of host cell lysis, Trends in Microbiology, vol. 8 No. 3, Mar. 2000, pp. 120-127.

Corbel, et al., Soluble antigens obtained from influenza virus by treatment with non-ionic detergent, J Hyg.,Camb., 1970, pp. 81-96, vol. 68.

Croux, et al., Interchange of functional domains switches enzymes specificity: construction of a chimeric pneumococcal-clostridial cell wall lytic enzyme, Molecular Microbiology, 1993, pp. 1019-1025, vol. 9, No. 5.

Diaz, et al., Chimeric phage-bacterial enzymes: a clue to the modular evolution of genes, Proc. Natl. Acad. Sci. USA, Oct. 1990, pp. 8125-8129, vol. 87.

Diaz, et al., Chimeric pneumococcal cell wall lytic enzymes reveal important physiological and evolutionary traits, Journal of Biological Chemistry, Mar. 25, 1991, pp. 5464-5471, vol. 266, No. 9.

Dixon, et al., Lysostaphin: an enzymatic approach to staphylococcal disease. III. Combined lysostaphin-methicillin therapy of established staphylococcal abcesses in mice, The Yale Journal of Biology and Medicine, Aug. 1968, pp. 62-68, vol. 41, No. 1.

Fischetti, et al., Size variation of the M protein in group A streptococci, Journal of Exp. Med., Jun. 1, 1985, pp. 1384-1401, vol. 161, No. 6.

Garcia, et al., Bacteriophages of Streptococcus pneumoniae: A molecular approach, Microbial Drug Resistance, Summer 1997, pp. 165-176, vol. 3, No. 2.

Garcia, et al., Cloning, purification and biochemical characterization of the pneumococcal bacteriophage Cp-1 lysin, Journal of Virology, Aug. 1987, pp. 2573-2580, vol. 61, No. 8.

Garcia, et al., Modular organization of the lytic enzymes of streptococcus pneumoniae and its bacteriophages, Gene, 1990, pp. 81-88, vol. 86.

Gerardy-Schann, et al., Molecular cloning and functional expression of bacteriophage PK1E-encoded endoneuraminidase Endo NE, Molecular Microbiology, May 1995, pp. 441-450, vol. 16, No. 3.

Goldberg, et al., Studies in experimental staphylococcal endocarditis in dogs, Antimicrobial Agents and Chemotherapy, 1967, pp. 45-53.

Harrison, et al., Lysostaphin in experimental renal infections, Journal of Bacteriology, Feb. 1967, pp. 520-524, vol. 93, No. 2.

Harrison, et al., Therapeutic activity of lysostaphin in experimental staphylococcal infections, Canadian Journal of Microbiology, Jan. 1967, pp. 93-97, vol. 13, No. 1.

Hayashi, et al., Effects of N-Acetylmuramidase from Streptomyces rutgersensis H-46 as a food preservative, Agric. Biol. Chem., Dec. 1989, pp. 3173-3177, vol. 53, No. 12.

Hayashida, et al., Further characterization of PL-1 phage associated N-acetylmuramidase of Lactobacillus casei, Journal of General Microbiology, May 1987, pp. 1343-1349, vol. 133, No. 5.

Higuchi, et al., Transfection of streptococcus sanguis by phage deoxyribonucleic acid isolated from streptococcus mutans, Infection and Immunity, Mar. 1977, pp. 945-949, vol. 15, part 3.

Huan, et al., Methicillin-resistant staphylococcus aureus infection and its treatment in burned patients, Chinese Journal of Surgery, 1994, vol. 32, No. 4, abstract.

Hughey, et al., Antimicrobial activity of lysozome against bacteria involved in food spoilage and food-borne disease, Applied and Enviromental Microbiology, Sep. 1987, pp. 2165-2170, vol. 53, No. 9.

Kohler, Systemic therapy with aerosols Aerosols in Medicine: Principles, Diagnosis and Therapy, 1993, Elseveir Science Publishers, pp. 303-319.

Lawman, et al., Molecular cloning of the extracellular endodextranase of streptococcus salivarius, Journal of Bacteriology, Dec. 1991, pp. 7423-7428, vol. 173, No. 23.

Loessner, et al., Evidence for a holin-like protein gene fully embedded out of frame in the endolysin gene of staphylococcus aureus bacteriophage 187, Journal of Bacteriology, Aug. 1999, pp. 4452-4460, vol. 181, No. 15.

Loessner, et al., Modified listeria bacteriophage lysin genes (ply) allow efficient overexpression and one—step purification of biochemically active fusion proteins, Applied and Environmental Microbiology, Aug. 1996, pp. 3057-3060, vol. 62, No. 8.

Lopez, et al., Architecture and domain interchange of the pneumococcal cell wall lytic enzymes, Genetics of Streptococci, Enterococci and Lactococci, Developments in Biological Standardization, 1995, pp. 273-281, vol. 85.

Lopez, et al., The pneumococcal cell wall degrading enzymes a modular design to create new lysins, Microbial Drug Resistance, Nov. 2, 1997, pp. 199-211, vol. 3, No. 2.

Martin, et al., Functional analysis of the two-gene lysis system of the pneumococcal phage Cp-1 in homologous and heterologous host cells, Journal of Bacteriology, Jan. 1998, pp. 210-217, vol. 180, No. 2.

Mukhlis, et al., Characterization and Immunogenicity of HSV-1 antigens obtained following zwitteronic detergent treatment; Vaccine, Sep. 1986, pp. 191-196, vol. 4.

Nelson, et al., Prevention and elimination of upper respiratory colonization of mice by group A streptococci by using a bacteriophage lytic enzyme, PNAS, Mar. 27, 2001, pp. 4107-4112, vol. 98, No. 7.

Nelson, et al., Selective and rapid killing of group A streptococci using a muralytic enzyme, Database Biosis Online, Biosciences Information Service, Philadelphia, PA, US and abstracts of the General Meeting of the American Society for Microbiology, 2000, pp. 32-33.

Oki, et al., Functional and structural features of the holin HOL protein of the Lactobacillus plantarum phage analysis in *escherichia coli* system, Gene, 1997, pp. 137-145, vol. 197.

Okuhara, et al., Preparation of group A streptococcal cell membranes by treatment with group C streptococcus phage—associated lysin, Annales Paediatrici Japonici, Jun. 1983, pp. 10-19, vol. 29, No. 2.

Patton, et al., Routes of delivery: case studies, Pulmonary delivery of peptides and proteins for systemic action, Advanced Drug Delivery Reviews, 1992, pp. 179-196, vol. 8.

Polak, et al., In vitro activity of recombinant lysostaphin-antibiotic combinations toward methicillin-resistant staphyococcus aureus, Diagn. Microbiol. Infect. Dis., 1993, pp. 265-270, vol. 17.

Raina, Purification of streptococcus group C bacteriophage lysin, Journal of Bacteriology, Jan. 1981, pp. 661-683, vol. 145, No. 1.

Ronda, et al., Infection of streptococcus oralis NCTC 11427 by pneomococcal phages, FEMS Microbiology Letters, 1989, pp. 187-192, vol. 65.

Sanz, et al., Construction of a multifunctional pneumococcal murein hydrolase by module assembly, Eur. J. Biochem., Feb. 1, 1996, pp. 601-605, vol. 235, No. 3.

Sato, et al., Partial characterization of n—Butanol—solubilized rejection—type antigens of syngeneic murine colon tumors, JNCI, Apr. 1985, vol. 74, No. 4.

Sheehan, et al., Analysis of the catylytic domain of the lysin of the lactococcal bacteriophage Tuc2009 by chimeric gene assembling; FEMS Microbiology Letters, 1996. pp. 23-28, vol. 140.

Sheehan, et al., The lytic enzyme of the pneumococcal phage Dp-1: A chimeric lysin of intergeneric orgin, Molecular Microbiology, 1997, pp. 717-725.

Witte, et al., Characterization of *escherichia coli* lysis using a family of chimeric E-L genes, FEMS Microbiology Letters, 1998, pp. 159-167, vol. 164.

Yarnall, et al., Isolation and partial characterization of a type II Fc receptor from a group A streptococcus, Molecular and Cellular Biochemistry, 1986, pp. 57-66, vol. 70.

Cisani, et al., High-level potentiation of lysostaphin antistaphylococcal activity by lysozome, Antimicrobial Agents and Chemotherapy, Apr. 1982, pp. 531-535, vol. 21, No. 4.

* cited by examiner

SYRUP COMPOSITION CONTAINING PHAGE ASSOCIATED LYTIC ENZYMES

The following application is a continuation of application Ser. No. 09/482,992, filed Jan. 14, 2000, now U.S. Pat. No. 6,264,945, and is a continuation-in-part of application Ser. No. 09/752,731, filed Jan. 3, 2001, now abandoned.

BACKGROUND OF THE INVENTION

1. Field of the Invention

The present invention discloses a method and composition for the treatment of bacterial infections by the parenteral introduction of a lysing enzyme blended with an appropriate carrier into a patient. The injection can be done intramuscularly, subcutaneously, or intravenously.

2. Description of the Prior Art

In the past, antibiotics have been used to treat various infections. The work of Selman Waksman in the introduction and production of Streptomycetes, and Dr. Fleming's discovery of penicillin, as well as the work of numerous others in the field of antibiotics, are well known. Over the years, there have been additions and chemical modifications to the "basic" antibiotics in attempts to make them more powerful, or to treat people allergic to these antibiotics.

Others have found new uses for these antibiotics. U.S. Pat. No. 5,260,292 (Robinson et al.) discloses the topical treatment of acne with aminopenicillins. The method and composition for topically treating acne and acneiform dermal disorders includes applying an amount of an antibiotic, effective for treating acne and acneiform dermal disorders, selected from the group consisting of ampicillin, amoxicillin, other aminopenicillins, and cephalosporins, and derivatives and analogs thereof. U.S. Pat. No. 5,409,917 (Robinson et al.) discloses the topical treatment of acne with cephalosporins.

However, as more antibiotics have been prescribed or used at an ever increasing rate for a variety of illnesses, increasing numbers of bacteria have developed a resistance to antibiotics. Larger doses of stronger antibiotics are now being used to treat ever more resistant strains of bacteria. Consequently, multiple antibiotic resistant bacteria have been developed. The use of more antibiotics and the number of bacteria showing resistance has led to increases in the amount of time that the antibiotics need to be used. Broad, non-specific antibiotics, some of which have detrimental effects on the patient, are now being used more frequently. Additionally, the number of people showing allergic reactions to antibiotics appears to be increasing.

Consequently, other efforts have been sought to first identify and then kill bacteria.

Attempts have been made to treat bacterial diseases with by the use of bacteriophages. U.S. Pat. No. 5,688,501 (Merril, et al.) discloses a method for treating an infectious bacterial disease with lytic or non-lytic bacteriophages that are specific for particular bacteria.

U.S. Pat. No. 4,957,686 (Norris) discloses a procedure of improved dental hygiene which comprises introducing into the mouth bacteriophages parasitic to bacteria which possess the property of readily adhering to the salivary pellicle.

It is to be noted that the direct introduction of bacteriophages into an animal to prevent or fight diseases has certain drawbacks. Specifically, the bacteria must be in the right growth phase for the phage to attach. Both the bacteria and the phage have to be in the correct and synchronized growth cycles. Additionally, there must be the right number of phages to attach to the bacteria; if there are too many or too few phages, there will either be no attachment or no production of the lysing enzyme. The phage must also be active enough. The phages are also inhibited by many things including bacterial debris from the organism the phages are going to attack. Further complicating the direct use of bacteriophage is the possibility of immunological reactions, rendering the phage non-functional.

Consequently, others have explored the use of other safer and more effective means to treat and prevent bacterial infections.

One bacteria for which a more effective treatment has been extensively explored is *Streptococcus*. The genus *Streptococcus* is comprised of a wide variety of both pathogenic and commensal gram-positive bacteria which are found to inhabit a wide range of hosts, including humans, horses, pigs, and cows. Within the host, streptococci are often found to colonize the mucosa surfaces of the mouth, nares and pharynx. However, in certain circumstances, they may also inhabit the skin, heart or muscle tissue.

Pathogenic streptococci of man include *S. pyogenes, S. pneumoniae*, and *S. faecalis*. While Group A streptococci may be present in the throat or on the skin and cause no symptoms of disease, they may also cause infections that range from mild to severe, and even life-threatening. Among the pathogenic hemolytic streptococci, *S. pyogenes*, or group A streptococci have been implicated as the etiologic agent of acute pharyngitis ("strep throat"), impetigo, rheumatic fever, scarlet fever, glomerulonephritis, and invasive fasciitis. Necrotizing fasciitis (sometimes described by the media as "the flesh-eating bacteria") is a destructive infection of muscle and fat tissue. Invasive group A streptococcal infections occur when the bacteria get past the defenses of the person who is infected. About 10,000–15,000 cases of invasive GAS disease occur in the United States each year, resulting in over 2,000 deaths. CDC estimates that 500 to 1,500 cases of necrotizing fasciitis and 2,000 to 3,000 cases of streptococcal toxic shock syndrome occur each year in the United States. Approximately 20% of patients with necrotizing fasciitis die, and 60% of patients with streptococcal toxic shock syndrome die. About 10 to 15% of patients with other forms of invasive group A streptococcal disease die.

Additionally, Group C *Streptococcus* can cause cellulitis from skin breaks, although cellulitis is normally associated with *Staphylococcus aureus*. Cellulitis can result in death, particularly in older individuals or in individuals who are already weakened.

Reports have described the characteristics of an enzyme produced by the group C streptococcal organism after being infected with a particular bacteriophage identified as C1 (Maxted, W. R. "The Active Agent in Nascent Page Lywsis of Streptococci," J. Gen Micro., vol 16, pp 585–595, 1957, Krause, R. M., "Studies on the Bacteriophages of Hemolytic Streptococci," J. Exp. Med, vol. 108, pp 803–821, 1958) and Fischetti, (Fischetti, V. A., et al, "Purification and Physical Properties of Group C Streptococcal Phage Associated Lysin," J. Exp. Med, Vol 133 pp. 1105–1117, 1971). The enzyme was given the name lysin and was found to specifically cleave the cell wall of group A, group C, and group E streptococci. These investigators provided information on the characteristics and activities of this enzyme with regard to lysing the group A streptococci and releasing the cell wall carbohydrate.

U.S. Pat. No. (application Ser. No. 08/962,523)(Fischetti, et. al.) and U.S. Pat. No. (application Ser. No. 09/257,026) (Fischetti et al.) disclose the use of an oral delivery mode, such as a candy, chewing gum, lozenge, troche, tablet, a powder, an aerosol, a liquid or a liquid spray, containing a lysin enzyme produced by group C streptococcal bacteria infected with a C1 bacteriophage for the prophylactic and therapeutic treatment of Streptococcal A throat infections, commonly known as strep throat.

U.S. Pat. No. 6,056,954 Fischetti and Loomis discloses a method for the prophylactic and therapeutic treatment of bacterial infections, which comprises the treatment of an individual with an effective amount of a lytic enzyme composition specific for the infecting bacteria, and a carrier for delivering said lytic enzyme. The methods disclosed included the topical, oral, and respiratory methods of delivering the enzyme. Another method disclosed in that application includes the use of suppositories. These methods and compositions can be used for the treatment of upper respiratory infections, skin infections, wounds and burns, vaginal infections, eye infections, intestinal disorders, and dental problems.

U.S. Pat. No. 6,056,955 (Fischetti and Loomis) discloses a method and composition for the topical treatment of streptococcal infections by the use of a lysin enzyme blended with a pharmaceutically acceptable carrier suitable for topical application to dermal tissues. The method for the treatment of dermatological streptococcal infections comprises administering a composition comprising effective amount of a therapeutic agent, with the therapeutic agent comprising a lysin enzyme produced by group C streptococcal bacteria infected with a C1 bacteriophage. The therapeutic agent can be in a pharmaceutically acceptable carrier.

The use of phage associated lytic enzymes produced by the infection of a bacteria with a bacteria specific phage has numerous advantages for the treatment of diseases. As the phage are targeted for specific bacteria, the lytic enzymes do not interfere with normal flora. Also, lytic phages primarily attack cell wall structures which are not affected by plasmid variation. The actions of the lytic enzymes are fast and do not depend on bacterial growth.

However, sometimes the bacterial infections, by the time they are treated, have developed into more serious illnesses. For example, dermatological infections such as *Staphylococcus aureus* and Streptococcal pneumoniae can develop into cellulitis, which, unchecked, can lead to a degradation of the connective tissue, septicemia, and possibly death. Other bacterial infections can also evolve into deep tissue infections. Other infections by other bacteria, not necessarily dermatological by nature, can infect and localize in certain tissues of the body, making the infections difficult to treat.

SUMMARY OF THE INVENTION

The present invention discloses the use of a variety of bacterial phage associated lytic enzymes for the treatment of a wide variety of illnesses caused by bacterial infections. More specifically, the present invention discloses the PARENTERAL application of a bacterial lytic enzyme, wherein the phage associated lytic enzyme is administered intramuscularly, subdermally, subcutaneously, or intravenously to treat a bacterial infection.

It is another object of the invention to apply a phage associated lytic enzyme intravenously, to treat septicemia and general infections.

It is also an object of the invention to inject a phage associated lytic enzyme into the tissue of an organism to treat a deep tissue infection.

It is also an object of the invention to administer a phage associated lytic enzyme intravenously.

The invention (which incorporates U.S. Pat. No. 5,604, 109 in its entirety by reference) uses an enzyme produced by the bacterial organism after being infected with a particular bacteriophage as a therapeutic treatment for those who have already become ill from the infection. The present invention is based upon the discovery that phage lytic enzymes specific for bacteria infected with a specific phage can effectively and efficiently break down the cell wall of the bacterium in question. At the same time, the semipurified enzyme is lacking in proteolytic enzymatic activity and therefore non-destructive to mammalian proteins and tissues when present during the digestion of the bacterial cell wall.

In one embodiment of the invention, the treatments of a variety of illnesses caused by *Streptococcus fasciae*, and *Staphylococcus aureus* are disclosed.

In yet another embodiment of the invention, lysostaphin, the enzyme which lyses *Staphylococcus aureus*, can be included in the therapeutic agent.

In a further embodiment of the invention, conventional antibiotics may be included in the therapeutic agent with the lytic enzyme, and with or without the presence of lysostaphin.

In another embodiment of the invention, more than one lytic enzyme may also be included in the therapeutic agent.

The therapeutic agent may be given parenterally, by means of an intramuscular, intradermal, or subcutaneous injection, or the agent may be given intravenously.

DETAILED DESCRIPTION OF THE INVENTION

The method for treating systemic or tissue bacterial infections comprises parenterally treating the infection with a therapeutic agent comprising an effective amount of at least one lytic enzyme produced by a bacteria infected with a bacteriophage specific for the bacteria, and an appropriate carrier.

The composition may be used for the therapeutic treatment of *Pseudomonas, Clostridium, Staphylococcus* infections, among others. These and other bacteria can be infected with bacteriophage specific for said bacteria, whereupon a lytic enzyme is produced specific for the lysing of that bacteria. For example, the composition which may be used for the therapeutic treatment of a strep infection includes the lysin enzyme and a means of application. When group C Streptococci are infected with a C1 bacteriophage, a lysin enzyme is produced specific for the lysing of *Streptococcus* group A.

A number of different bacteria may be treated. Among the bacteria which most often infect deep tissues, and, more specifically connective tissues, are Group A *Streptococcus, Staphylococcus, Pseudomonas,* and *Clostridium*. More than one lytic enzyme may be introduced into the infected body at a time.

A number of different methods may be used to introduce the lytic enzyme(s). These methods include introducing the lytic enzyme intravenously, intramuscularly, subcutaneously, and subdermally.

In one preferred embodiment of the invention, a deep tissue infection may be treated by injecting into the infected tissue of the patient a therapeutic agent comprising the appropriate lytic enzyme(s) and a carrier for the enzyme. The carrier may be comprised of distilled water, a saline solution, albumin, a serum, or any combinations thereof. More specifically, solutions for infusion or injection may be prepared in a conventional manner, e.g. with the addition of preservatives such as p-hydroxybenzoates or stabilizers such as alkali metal salts of ethylene-diamine tetraacetic acid, which may then be transferred into fusion vessels, injection vials or ampules. Alternatively, the compound for injection may be lyophilized either with or without the other ingredients and be solubilized in a buffered solution or distilled water, as appropriate, at the time of use. Non-aqueous vehicles such as fixed oils and ethyl oleate are also useful herein.

In cases where intramuscular injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. The pharmaceutical preparations according to the present invention are provided sterile and pyrogen free.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counterions such as sodium; non-ionic surfactants such as polysorbates, poloxamers, or polyethylene glycol (PEG); and/or neutral salts, e.g., NaCl, KCl, MgCl.sub.2, CaCl.sub.2, etc.

Glycerin or glycerol (1,2,3-propanetriol) is commercially available for pharmaceutical use. It may be diluted in sterile water for injection, or sodium chloride injection, or other pharmaceutically acceptable aqueous injection fluid, and used in concentrations of 0.1 to 100% (v/v), preferably 1.0 to 50% more preferably about 20%.

DMSO, which is an aprotic solvent with a remarkable ability to enhance penetration of many locally applied drugs. DMSO may be diluted in sterile water for injection, or sodium chloride injection, or other pharmaceutically acceptable aqueous injection fluid, and used in concentrations of 0.1 to 100% (v/v).

The carrier vehicle may also include Ringer's solution, a buffered solution, and dextrose solution, particularly when an intravenous solution is prepared.

Prior to, or at the time the lysin enzyme is put in the carrier system or oral delivery mode, it is preferred that the enzyme be in a stabilizing buffer environment for maintaining a pH range between about 4.0 and about 9.0, more preferably between about 5.5 and about 7.5 and most preferably at about 6.1. This is pH range is most suitable for the lysin enzyme for Streptococcus.

The stabilizing buffer should allow for the optimum activity of the lysin enzyme. The buffer may be a reducing reagent, such as dithiothreitol. The stabilizing buffer may also be or include a metal chelating reagent, such as ethylenediaminetetracetic acid disodium salt, or it may also contain a phosphate or citrate-phosphate buffer. The buffers found in the carrier can serve to stabilize the environment for the lytic enzymes.

The effective dosage rates or amounts of the lytic enzyme to treat the infection, and the duration of treatment will depend in part on the seriousness of the infection, the duration of exposure of the recipient to the infectious bacteria, the number of square centimeters of skin or tissue which are infected, the depth of the infection, the seriousness of the infection, and a variety of a number of other variables. The composition may be applied anywhere from once to several times a day, and may be applied for a short or long term period. The usage may last for days or weeks. Any dosage form employed should provide for a minimum number of units for a minimum amount of time. The concentration of the active units of enzyme believed to provide for an effective amount or dosage of enzyme may be in the range of about 100 units/ml to about 500,000 units/ml of composition, preferably in the range of about 1000 units/ml to about 100,000 units/ml, and most preferably from about 10,000 to 100,000 units/ml. The amount of active units per ml and the duration of time of exposure depends on the nature of infection, and the amount of contact the carrier allows the lytic enzyme to have. It is to be remembered that the enzyme works best when in a fluid environment. Hence, effectiveness of the enzyme is in part related to the amount of moisture trapped by the carrier. For the treatment of septicemia, there should be a continuous intravenous flow of therapeutic agent into the blood stream. The concentration of lytic enzyme for the treatment of septicemia is dependent upon the seriousness of the infection.

In order to accelerate treatment of the infection, the therapeutic agent may further include at least one complementary agent which can also potentiate the bactericidal activity of the lytic enzyme. The complementary agent can be penicillin, synthetic penicillins bacitracin, methicillin, cephalosporin, polymyxin, cefaclor. Cefadroxil, cefamandole nafate, cefazolin, cefixime, cefmetazole, cefonioid, cefoperazone, ceforanide, cefotanme, cefotaxime, cefotetan, cefoxitin, cefpodoxime proxetil, ceftazidime, ceftizoxime, ceftriaxone, cefriaxone moxalactam, cefuroxime, cephalexin, cephalosporin C, cephalosporin C sodium salt, cephalothin, cephalothin sodium salt, cephapirin, cephradine, cefuroximeaxetil, dihydratecephalothin, moxalactam, loracarbef, mafate, chelating agents and any combinations thereof in amounts which are effective to synergistically enhance the therapeutic effect of the lytic enzyme.

Additionally, the therapeutic agent may further comprise the enzyme lysostaphin for the treatment of any *Staphylococcus aureus* bacteria. Mucolytic peptides, such as lysostaphin, have been suggested to be efficacious in the treatment of *S. aureus* infections of humans (Schaffner et al., Yale J. Biol. & Med., 39:230 (1967) and bovine mastitis caused by *S. aureus* (Sears et al., J. Dairy Science, 71 (Suppl. 1): 244(1988)). Lysostaphin, a gene product of *Staphylococcus simulans,* exerts a bacteriostatic and bactericidal effect upon *S. aureus* by enzymatically degrading the polyglycine cross-link of the cell wall (Browder et al., Res. Comm., 19: 393–400 (1965)). U.S. Pat. No. 3,278,378 describes fermentation methods for producing lysostaphin from culture media of *S. staphylolyticus*, later renamed *S. simulans*. Other methods for producing lysostaphin are further described in U.S. Pat. Nos. 3,398,056 and 3,594,284. The gene for lysostaphin has subsequently been cloned and sequenced (Recsei et al., Proc. Natl. Acad. Sci. USA, 84: 1127–1131 (1987)). The recombinant mucolytic bactericidal protein, such as r-lysostaphin, can potentially circumvent problems associated with current antibiotic therapy because of its targeted specificity, low toxicity and possible reduction of biologically active residues. Furthermore, lysostaphin is also active against non-dividing cells, while most antibiotics require actively dividing cells to mediate their effects (Dixon et al., Yale J. Biology and Medicine, 41: 62–68 (1968)).

Lysostaphin, in combination with the lysin enzyme, can be used in the presence or absence of the listed antibiotics. There is a degree of added importance in using both lysostaphin and the lysin enzyme in the same therapeutic agent. Frequently, when a body has a bacterial infection, the infection by one genus of bacteria weakens the body or changes the bacterial flora of the body, allowing other potentially pathogenic bacteria to infect the body. One of the bacteria that sometimes co-infects a body is *Staphylococcus aureus*. Many strains of *Staphylococcus aureus* produce penicillinase, such that *Staphylococcus, Streptococcus,* and other gram positive bacterial strains will not be killed by standard antibiotics. Consequently, the use of the lysin and lysostaphin, possibly in combination with antibiotics, can serve as the most rapid and effective treatment of bacterial infections. In yet another preferred embodiment, the invention may include mutanolysin, and lysozyme Many modifications and variations of the present invention are possible in light of the above teachings. It is, therefore, to be understood within the scope of the appended claims the invention may be protected otherwise than as specifically described.

What we claim is:

1. A parenteral therapeutic agent for the treatment of bacterial infections comprising:
    a) an effective amount of at least one enzyme genetically coded for by at least one specific bacteriophage specific for a specific bacteria, wherein said at least one enzyme is selected fro the group consisting of at least one unaltered lytic enzyme, at least one shuffled lytic enzyme, at least one chimeric lytic enzyme at least one holin protein, and combinations thereof, said at least one enzyme having the ability to digest a cell wall of a specific said bacteria;
    b) a parenteral carrier for the parenteral delivery of said at least one lytic enzyme to the site of the infection, said parenteral carrier comprising:
        i) a fluid selected from the group consisting of distilled water, a saline solution, albumin, a serum, and any combinations thereof;
        ii) supplemental additive selected from the group consisting of saline, buffer, and combinations thereof; and
        iii) nutritional agents selected from the group consisting of dextrose, mannitol, sorbitol, lactose, gelatin, and combinations thereof.

2. The parenteral therapeutic agent according to claim 1, comprising a vasoconstriction agent.

3. The parenteral therapeutic agent according to claim 1, wherein the at least one said enzyme is for the treatment of *Pseudomonas*.

4. The parenteral therapeutic agent according to claim 1, wherein the at least one said enzyme is for the treatment of *Streptococcus*.

5. The parenteral therapeutic agent according to claim 1, wherein the at least one said enzyme is for the treatment of *Staphylococcus*.

6. The parenteral therapeutic agent according to claim 1, wherein the at least one said enzyme is for the treatment of *Clostridium*.

7. The parenteral therapeutic agent according to claim 1, wherein said agent further comprises a buffer that maintains pH of the composition at a range between about 4.0 and about 9.0.

8. The parenteral therapeutic agent according to claim 7, wherein the buffer maintains the pH of the composition at the range between about 5.5 and about 7.5.

9. The parenteral therapeutic agent according to claim 1, wherein said buffer comprises a reducing reagent.

10. The parenteral therapeutic agent according to claim 9, wherein said reducing reagent is dithiothreitol.

11. The parenteral therapeutic agent according to claim 1, wherein said buffer comprises a metal chelating reagent.

12. The parenteral therapeutic agent according to claim 11, wherein said metal chelating reagent is ethylenediaminetetracetic disodium salt.

13. The parenteral therapeutic agent according to claim 1, wherein said buffer is a citrate-phosphate buffer.

14. The parenteral therapeutic agent according to claim 1, further comprising a bactericidal or bacteriostatic agent as a preservative.

15. The parenteral therapeutic agent according to claim 1, further comprising a concentration of about 100 to about 500,000 active enzyme units per milliliter of fluid in the wet environment of the nasal or oral passages.

16. The parenteral therapeutic agent according to claim 1, wherein said therapeutic agent is an intravenous therapeutic agent.

17. The parenteral therapeutic agent according to claim 1, wherein said therapeutic agent is an intramuscular therapeutic agent.

18. The therapeutic agent according to claim 1, wherein said therapeutic agent is a subcutaneous therapeutic agent.

19. The composition according to any one of claims 1–18, further comprising a parenteral dispenser containing said parenteral therapeutic agent.

* * * * *